United States Patent [19]

Herd et al.

[11] Patent Number: 5,414,131
[45] Date of Patent: May 9, 1995

[54] PROCESS FOR PREPARING [5-AMINO-2-(2-HYDROXYETHYLAMINO)-PHENYL](2-HYDROXYETHYL)SULPHONE

[75] Inventors: Karl-Josef Herd, Odenthal; Hermann Henk, Cologne, both of Germany

[73] Assignee: Bayer Aktiengesellschaft, Leverkusen, Germany

[21] Appl. No.: 160,698

[22] Filed: Dec. 1, 1993

[30] Foreign Application Priority Data

Dec. 8, 1992 [DE] Germany .................. 42 41 284.6

[51] Int. Cl.⁶ .................. C07C 323/25; C07C 209/30
[52] U.S. Cl. .................. 564/440; 564/415; 534/566
[58] Field of Search .................. 564/415, 440; 534/566

[56] References Cited

U.S. PATENT DOCUMENTS

| | | | |
|---|---|---|---|
| 4,577,015 | 3/1986 | Jager et al. | 544/76 |
| 5,107,025 | 4/1992 | Herd | 564/440 |
| 5,278,291 | 1/1994 | Herd | 534/566 |

FOREIGN PATENT DOCUMENTS 431389 11/1990 European Pat. Off. .

OTHER PUBLICATIONS

Merck Index, 10th Edition, 1193, p. 168, 1983.

*Primary Examiner*—Shailendra Kumar
*Attorney, Agent, or Firm*—William C. Gerstenzans; Sprung Horn Kramer & Woods

[57] ABSTRACT

A process for preparing the sulphone of the formula

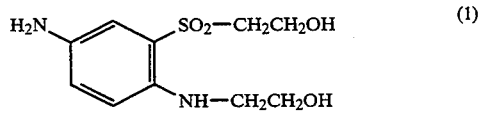

consists in reductive cleavage of disazo/disazoxy dyestuffs of the formula

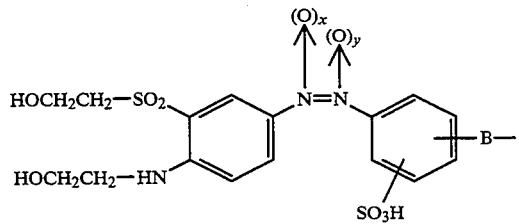

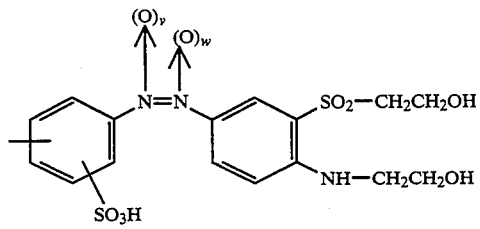

in which
  B is a direct bond or a bridging member and
  v, w, x, y, independently of one another, are 0 or 1, x+y being 0 or 1 and v+w being 0 or 1.

7 Claims, No Drawings

PROCESS FOR PREPARING [5-AMINO-2-(2-HYDROXYETHYLAMINO)-PHENYL](2-HYDROXYETHYL)SULPHONE

[5-Amino-2-(2-hydroxyethylamino)phenyl](2-hydroxyethylsulphone of the formula (1) is an important intermediate in the synthesis of dyestuffs, in particular in the synthesis of reactive dyestuffs, as described, for example, in DE-A 3,512,340 or U.S. Pat. No. 4,577,015.

U.S. Pat. No. 5,107,025 describes a preparation process based on the catalytic reduction of monoazo/azoxy compounds. Removal of (1) and the particular diazo components to be reused in accordance with the process is not optimal. This is mainly due to the solubility product of the betaine of the diazo component in water.

Accordingly, the invention relates to a novel process for preparing [5-amino-2-(2-hydroxyethylamino)-phenyl]-(2-hydroxyethyl)sulphone of the formula (1)

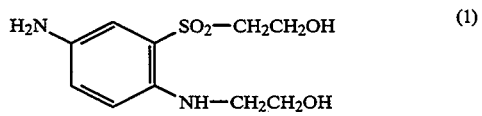

characterized in that disazo/disazoxy dyestuffs of the formula (5)

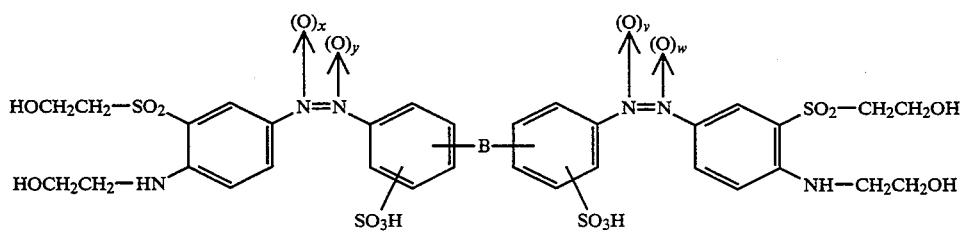

in which

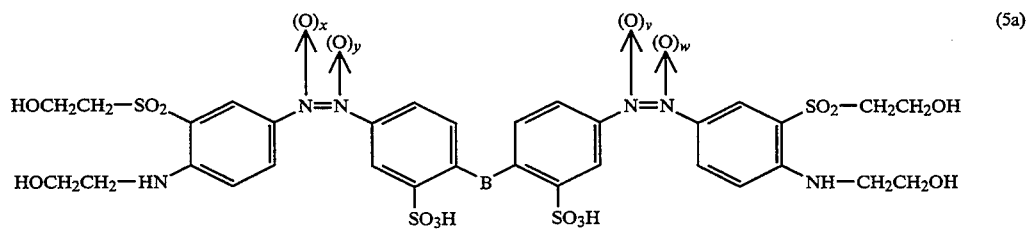

disazoxy dyestuffs of the formula (5a)

B is a direct bond or a bridging member, such as, for example, $CH_2$, $CH_2CH_2$, $SO_2$, $CO$, $O$, $CH=CH$, $NHCONH$, $OCH_2CH_2O$, $NH$ or $N(C_1-C_4\text{-alkyl})$, preferably $CH_2CH_2$ or $CH=CH$, and v, w, x, y, independently of one another, are 0 or 1, x+y being 0 or 1 and v+w being 0 or 1, are reductively cleaved to give the diamino compound of the formula (2)

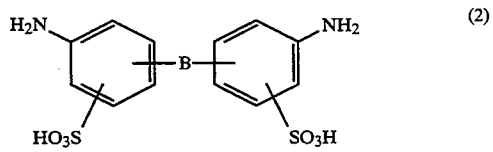

and 2 equivalents of the formula (1), and the resulting diamino compound of the formula (2), after acidification and precipitation, is separated off as a sparingly water-soluble doubled betaine, a sparingly water-soluble betaine being understood to mean one having a solubility of 0.0 g/l to 1 g/l (25° C.).

The almost quantitatively precipitated and removed (2) is reused in the synthesis. The compound of the formula (1) which remains in solution can either be isolated by concentrating or else directly further reacted in this form.

The reduction of the disazo/disazoxy dyestuffs of the formula (5) to (1) and (2) can take place by methods such as described in U.S. Pat. No. 5,107,025 and by R. Schröter in, Handbuch für preparative Methoden der organischen Chemie, Houben-Weyl, Volume XI, Part 1, page 522 to 531. According to these references, reduction with sodium dithionite or D-glucose or else catalytic reduction with hydrogen are particularly advantageous. Suitable catalysts for these reductions are in particular Raney nickel, palladium/carbon or platinum compounds. The reduction is preferably carried out in water at temperatures of between 20° and 80° C. and under neutral pH conditions, preferably between pH 5 to pH 8. Catalytic reduction with hydrogen is in general carried out at pressures of 10 to 100 atm, preferably 30 to 80 atm, in particular at 50 to 70 atm, in an autoclave suitable therefor.

In a particular embodiment of the process, disazo/- in which
B is $CH_2CH_2$ or $CH=CH$ and
v, w, x, y, independently of one another, are 0 or 1, v+w being 0 or 1 and x+y being 0 or 1,
are reduced to give (1) and diamino compounds of the formula (2a)

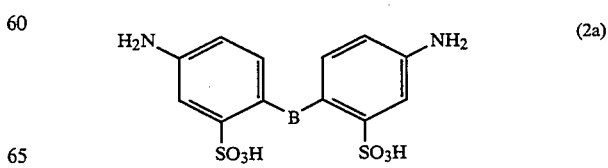

In a further particular embodiment of the process, the compounds of the formula (1) are obtained by reduction of the disazo/disazoxy dyestuffs of the formula (5), which in turn can be obtained by tetrazotizing diamino compounds of the formula (2)

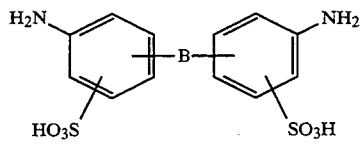 (2)

in which
B is a direct bond or a bridging member such as, for example, $CH_2$, $CH_2CH_2$, $SO_2$, CO, O, $CH=CH$, NHCONH, $OCH_2CH_2O$, NH or $N(C_1-C_4\text{-alkyl})$, coupling the tetrazoniumcompounds onto 2 equivalents of 2-(2-hydroxyethyl)mercapto-N-(2-hydroxyethyl)aniline of the formula (3)

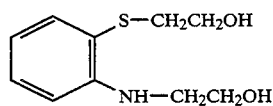 (3)

and oxidizing the resulting disazo compounds of the formula (4)

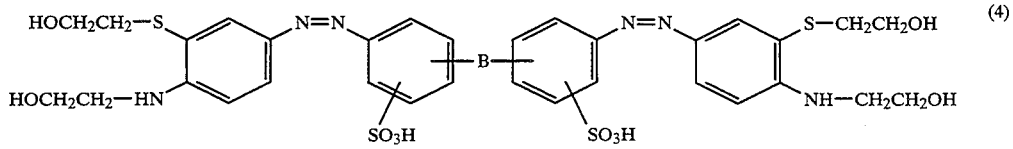 (4)

to disazo/disazoxy dyestuffs of the formula (5)

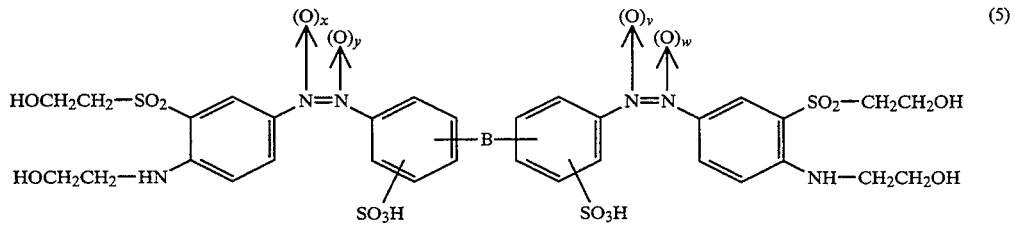 (5)

in which
v, w, x and y, independently of one another, are 0 or 1,
v+w being 0 or 1 and
x+y being 0 or 1.

A particular embodiment of this process consists in the use of diamino compounds of the formula (2a)

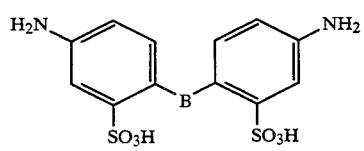 (2a)

in which
B is $CH_2-CH_2$ or $CH=CH$.

The doubled betaine of (2a) has only low water solubility of about 0.5 g/l at 25° C.

Sulpho-containing diamino compounds have the advantage that the process, i.e. diazotization, coupling, oxidation and reduction, can be carried out in an aqueous reaction medium. Azo coupling of tetrazotized diamino compounds (2) onto two equivalents (3) is preferably carried out at temperatures of between 0° and 30° C. and a pH of preferably 0.5 to 5.0. For this reaction the use of emulsifiers or coupling accelerators, such as, for example, urea, may be advantageous. Dyestuffs (4) are obtained as crystalline compounds and can therefore be isolated by filtration. Since the coupling reaction in most cases gives relatively uniform products, (4) can also be oxidized directly, without intermediate isolation, to give disazo/disazoxy dyestuffs (5).

The oxidizing agents used can be, for example, hydrogen peroxide, perborates, persulphates, persulphonic acids or peroxides of alkali metal and alkaline earth metals, if appropriate in the presence of suitable catalysts.

In a particularly preferred embodiment of the process, hydrogen peroxide in the presence of catalytic amounts (0.001 to 2% by weight, relative to (4)) of tungstates and/or vanadates, in particular alkali metal tungstates and/or alkali metal vanadates, has proven to be an advantageous oxidizing agent.

Oxidation is in general carried out in aqueous medium at 20° to 100° C., preferably 40° to 90° C., and at a pH of 4 to 8. The reaction passes through the corresponding sulphoxide compounds as intermediates.

The disazo/disazoxy dyestuffs (5) can be isolated as yellow to red crystalline compounds and can be additionally purified by recrystallization from water or water/alcohol mixtures.

After reduction, a two-component solution is obtained from which, after separating off the catalyst, the diamino compound (2) can be made to precipitate by acidification with mineral acids, such as, for example, sulphuric acid or hydrochloric acid and separated off almost quantitatively as doubled betaine by filtration or pressing. Compound (1) remains in the acid filtrate and can then be isolated or neutralized and directly further reacted as a solution. The removed diamino compound (2) can be tetrazotized and reused in the next synthesis sequence.

The formulae given for the intermediates and disazo dyestuffs are those of the free acids. In general, the salts are used or obtained in the preparation, in particular the alkali metal salts, such as, for example, sodium salts, potassium salts or lithium salts.

EXAMPLE 1

54 g of 4,4'-diaminostilbene-2,2'-disulphonic acid are stirred in 300 ml of water, 100 g of ice and 60 ml of conc. hydrochloric acid and then tetrazotized by addition of 70 ml of a 30% strength by volume aqueous sodium nitrite solution. The suspension is stirred at 5° C. for 1 hour. Excess nitrite is removed by addition of sulphamic acid after the reaction has ended. A solution of 65 g of 2-(2-hydroxyethylmercapto)-N-(2-hydroxyethyl)aniline in 50 ml of water/15 ml of conc. hydrochloric acid is then added. After 30 minutes, the pH is brought from 0.5–0.8 to 1.5 at about 10° C. over a period of 1 hour with sodium carbonate solution, and the resulting mixture is stirred for 2 hours. It is then stirred at 10° to 15° C. and pH 2.0 to 2.5 for 6 to 8 hours. The precipitated intermediate of the structure

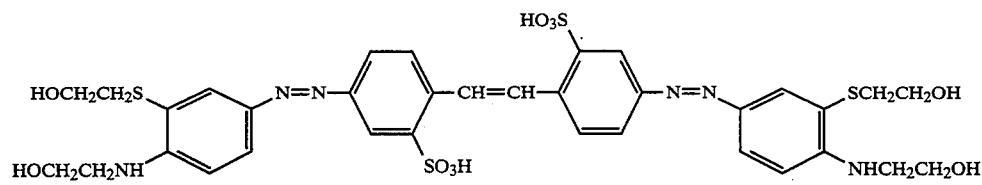

($\lambda_{max}$=481 nm) is isolated by suction filtration, and the moist paste is directly further reacted. However, isolation of the intermediate can also be dispensed with, and the coupling mixture can directly be oxidized.

For oxidation, the moist paste is suspended in 400 ml of water, the suspension is brought to pH 5.0 with sodium. carbonate solution, and 0.2 g of sodium tungstate is added. The reaction mixture is heated to 60° C. Without any further addition of heat, about 100 ml of a 30% strength aqueous hydrogen peroxide solution are then slowly metered in, as a result of which the temperature rises to about 70° to 75° C. owing to the heat of reaction and a solution is formed. During the reaction, the pH is kept constant at 5.0 with sodium carbonate solution. After an additional stirring phase of 1 hour at 75° C., the mixture is slowly cooled to 20° C. the precipitated dyestuff is isolated and dried to give about 100 g of a salt-containing product of the structure

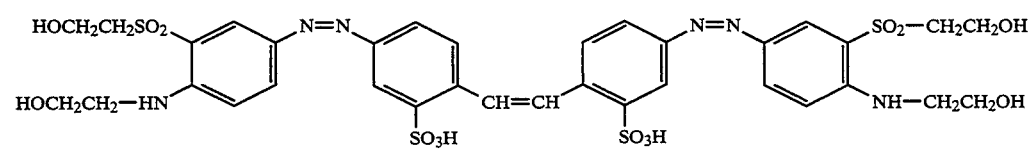

($\lambda_{max}$=440 nm (H$_2$O)), the structure given including possible disazoxy compounds. Drying can also be dispensed with, and the moist dyestuff paste can directly be further reacted by suspending it in 250 ml of water at pH 7, adding 0.2 g of Raney nickel catalyst, and reducing the mixture in an autoclave at 50 to 70 atm with 4.5 to 4.7 times the equimolar amount of hydrogen.

This may result in heating of the suspension to 40° to 50° C. After letdown and removal of the catalyst by filtration, a clear, pale brownish solution is obtained. It is heated to 60° C. and brought to a pH of 1.0 with dilute sulphuric acid. This results in almost quantitative crystallization of the 4,4'-diaminostilbene-2,2'-disulphonic acid as the betaine. It is filtered off with suction while Hot and washed with 50 ml of cold water. Drying gives about 40 g of 4,4'-diaminostilbene-2,2'-disulphonic acid.

The filtrate combined with the wash water contains the desired [5-amino-2-(2hydroxyethylamino)phenyl]-(2-hydroxyethyl) sulphone of the formula

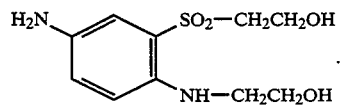

Content analysis of the 350 ml of solution is performed by means of diazotization. It shows that about 55 g of product of the above formula are in solution. Comparison by TLC shows that this compound is identical to a sample of the substance prepared by the method of EP 153,599. After neutralization, the above solution can be used for dyestuff synthesis.

EXAMPLE 2

54 g of 2,2'-(1,2-ethanediyl)bis[5-aminobenzenesulphonic acid] are stirred in 300 ml of water, 100 g of ice and 60 ml of conc. hydrochloric acid and then tetrazotized by addition of 70 ml of a 30% strength by volume aqueous sodium nitrite solution. The suspension is stirred at 5° C. for 1 hour. Excess nitrite is removed by addition of sulphamic acid after the reaction has ended. A solution of 65 g of 2-(2-hydroxyethylmercapto)-N-(2-hydroxyethyl)aniline in 50 ml of water/15 ml of conc. hydrochloric acid is then added. After 30 minutes, the pH is brought from 0.5–0.8 to 1.5 at about 10° C. over a period of 1 hour with sodium carbonate solution, and the resulting mixture is stirred for 2 hours. It is then stirred at 10° to 15° C. and pH 2.0 to 2.5 for 6 to 8 hours. The precipitated intermediate of the structure

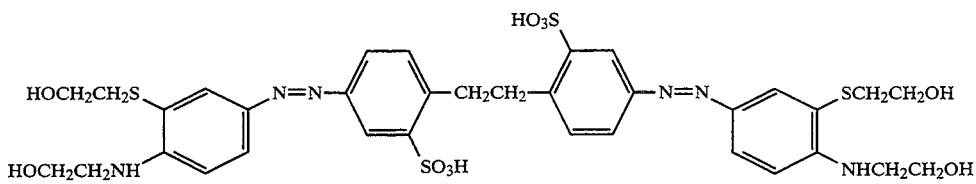

($\lambda_{max}$=440 nm) is isolated by suction filtration, and the moist paste is directly further reacted. However, isolation of the intermediate can also be dispensed with, and the coupling mixture can directly be oxidized by the following procedure:

For oxidation, the moist paste is suspended in 400 ml of water, the suspension is brought to pH of 6.5 with sodium carbonate solution, and 0.2 g of sodium tungstate is added. The reaction mixture is heated to 60° C. Without any further addition of heat, about 100 ml of a 30% strength aqueous hydrogen peroxide solution are then slowly metered in, as a result of which the temperature rises to about 70° to 75° C. owing to the heat of reaction and a solution is formed. During the reaction, the pH is kept constant at 5.0 with sodium carbonate solution. After an additional stirring phase of 1 hour at 75° C., the mixture is cooled to 20° C., the salted-out dyestuff is isolated and dried to give about 100 g of a salt-containing product of the structure

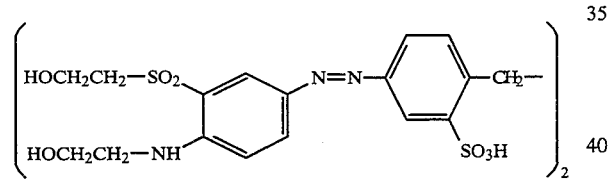

($\lambda_{max}$=395,435 (sh) nm ($H_2O$)), the structure given including possible disazoxy compounds.

Drying can also be dispensed with, and the moist paste can directly be further reacted.

The moist dyestuff paste is suspended in 250 ml of water, 0.2 g of Raney nickel catalyst is added, and the mixture is reduced in an autoclave at 50 to 70 atm with 4.5 to 4.7 times the equimolar amount of hydrogen.

This may result in exothermic heating of the suspension to 40° C. After the end of the reaction, the catalyst is filtered off, and the remaining aqueous solution is heated to 80° C. The pH is brought to 1.0 with dilute sulphuric acid, resulting in almost quantitative precipitation of the 2,2'-(1,2-ethanediyl)bis[5-aminobenzenesulphonic acid] as the dibetaine. It is filtered off with suction at 60° C. and washed with 50 ml of cold water. After tetrazotization, the removed diamino compound can be reused in the next synthesis sequence.

The filtrate combined with the wash water contains the desired [5-amino-2-(2-hydroxyethylamino)phenyl]-(2-hydroxyethyl) sulphone, which can now be analyzed and reacted as described in Example 1.

What is claimed is:

1. A process for preparing [5-amino-2-(2-hydroxyethylamino)phenyl] (2-hydroxyethyl)sulphone of the formula

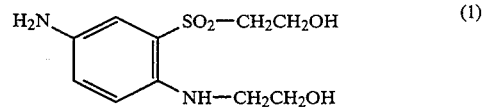

characterized in that a disazo/disazoxy dyestuff of the formula

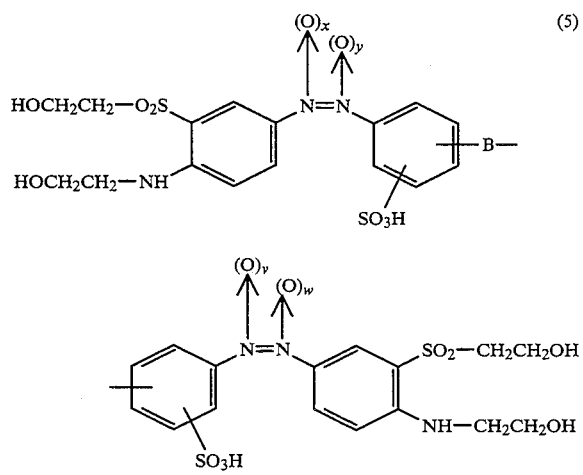

in which

B is a direct bond or bridging member and v, w, x and y, independently of one another, are 0 or 1, x+y being 0 or 1 and v+w being 0 or 1, are reductively cleaved, and the resulting diamino compound of the formula (2)

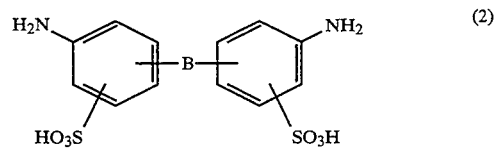

after acidification and precipitation, is separated off as a doubled, sparingly water-soluble betaine.

2. The process according to claim 1, characterized in that a disazo/disazoxy dyestuff of the formula (5) wherein B is $CH_2$, $CH_2CH_2$, $SO_2$, CO, O, CH=CH, NHCONH, $OCH_2CH_2O$, NH or N($C_1$-$C_4$-alkyl) is used.

3. The process according to claim 1, characterized in that a disazo/disazoxy dyestuff of the formula (5) wherein B is $CH_2CH_2$ or CH=CH is used.

4. The process according to claim 1, characterized in that a disazo/disazoxy dyestuff of the formula (5a)

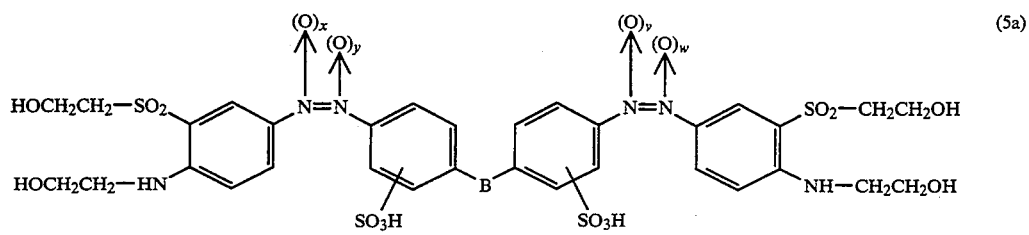

in which B is $CH_2CH_2$ or $CH=CH$ and v, w, x and y have the abovementioned meanings is used.

5. The process according to claim 1, characterized in that the disazo/disazoxy dyestuff of the formula (5) is obtained by tetraotizing diamino compounds of the formula

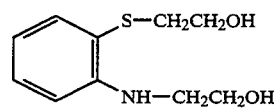

in which

B is a direct bond or a bridging member, coupling the tetrazonium compound onto 2 equivalents of 2-(2-hydroxyethyl)mercapto-N-(2-hydroxyethyl)-aniline of the formula

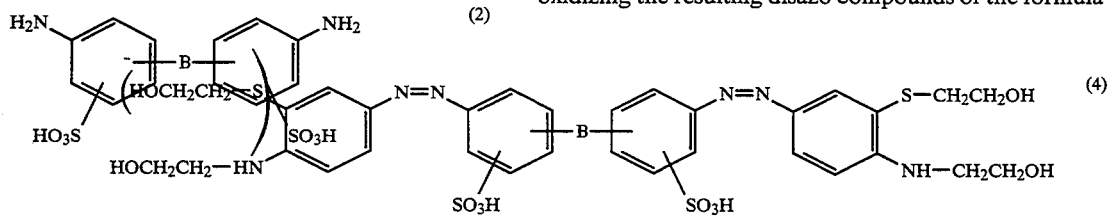

oxidizing the resulting disazo compounds of the formula

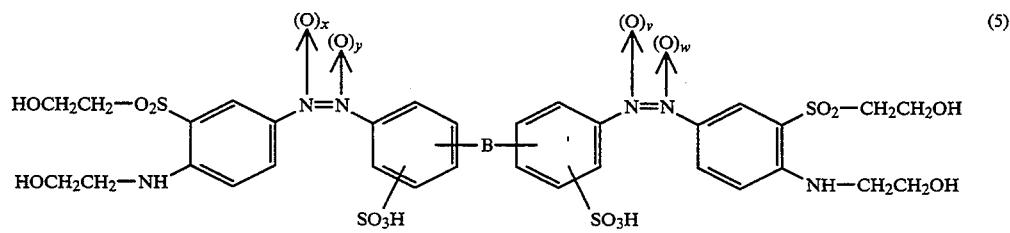

to disazo/disazoxy dyestuffs of the formula in which B, v, w, x and y have the abovementioned meanings.

6. The process according to claim 5, using diamino compounds where B is $CH_2$, $CH_2CH_2$, $SO_2$, CO, O, $CH=CH$, NHCONH, $OCH_2CH_2O$, NH or $N(C_1-C_4\text{-alkyl})$.

7. The process according to claim 5, using diamino compounds of the formula

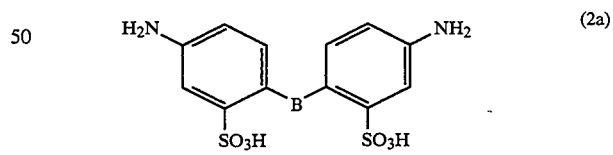

where B is $CH_2-CH_2$ or $CH=CH$.

* * * * *

UNITED STATES PATENT AND TRADEMARK OFFICE
CERTIFICATE OF CORRECTION

PATENT NO. : 5,414,131
DATED : May 9, 1995
INVENTOR(S) : Herd, et al.

It is certified that error appears in the above-indentified patent and that said Letters Patent is hereby corrected as shown below:

| | |
|---|---|
| Title Page | OTHER PUBLICATIONS: Insert --Chemical Abstract, Vol. 106, 1987, 106:121387 -- |
| Col. 9, Formula 2 | Formula (2) is mixed with Formula (4) delete " 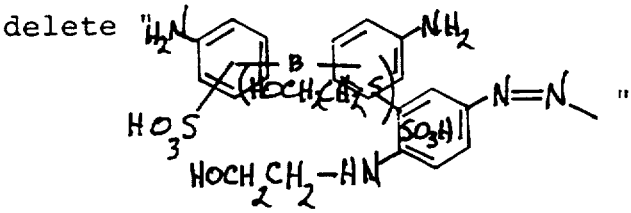 " and substitute 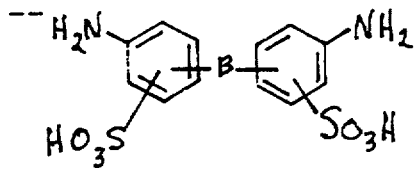 -- |
| Col. 10, Formula 4 | Formula (4) is mixed with Formula (2) delete " 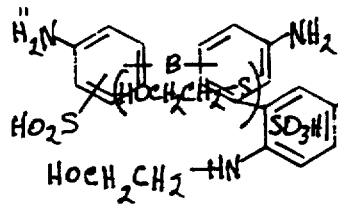 " and |

UNITED STATES PATENT AND TRADEMARK OFFICE
CERTIFICATE OF CORRECTION

PATENT NO. : 5,414,131

DATED : May 9, 1995

INVENTOR(S) : Herd, et al.

It is certified that error appears in the above-identified patent and that said Letters Patent is hereby corrected as shown below:

Col. 10, Formula 4 Cont'd    substitute

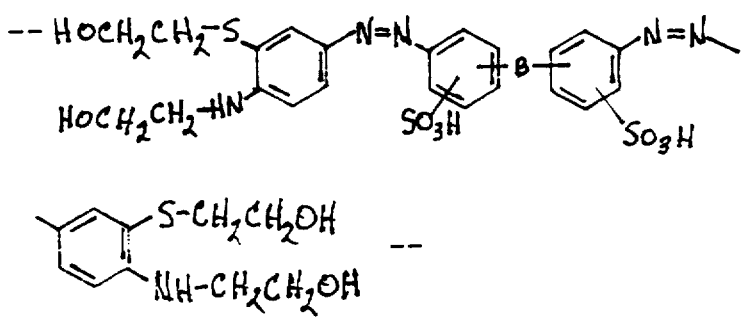

Signed and Sealed this

Twenty-third Day of April, 1996

Attest:

BRUCE LEHMAN

Attesting Officer

Commissioner of Patents and Trademarks